United States Patent [19]

Foà et al.

[11] Patent Number: 4,537,970
[45] Date of Patent: Aug. 27, 1985

[54] PROCESS FOR THE PREPARATION OF ESTERS OR SALTS OF AROMATIC OR ETHEROAROMATIC ACIDS

[75] Inventors: Marco Foà; Franco Francalanci, both of Novara; Andrea Gardano, Trino Vercellese; Elena Bencini, Novara, all of Italy

[73] Assignee: Montedison S.p.A., Milan, Italy

[21] Appl. No.: 560,228

[22] Filed: Dec. 12, 1983

[30] Foreign Application Priority Data

Dec. 14, 1982 [IT] Italy .................. 24723 A/82

[51] Int. Cl.$^3$ ............ C07D 239/02; C07C 67/36; C07C 51/10
[52] U.S. Cl. .................. 546/319; 260/465 D; 546/318; 546/327; 549/71; 549/484; 549/486; 560/19; 560/37; 560/51; 560/64; 560/67; 560/97; 560/100; 560/103; 562/406
[58] Field of Search .......... 562/406; 560/97, 100, 560/103, 114, 19, 37, 51, 64, 67; 260/465 D; 546/318, 319, 327; 549/71, 484, 486

[56] References Cited

U.S. PATENT DOCUMENTS 3,988,358 10/1976 Heck .................. 260/465 D
4,435,575 3/1984 Cainelli et al. .............. 562/406 X Primary Examiner—Dolph H. Torrence
Attorney, Agent, or Firm—Stevens, Davis, Miller & Mosher

[57] ABSTRACT

This invention relates to the preparation of esters or salts of aromatic or etheroaromatic acids having formula Y—Ar—CO—OR (I), where:
Ar represents an aromatic group constituted by one or more benzene rings, optionally condensed, or an etheroaromatic nucleus optionally condensed with one or more benzene rings;
Y represents from zero to more substituents, equal or different, chosen among a halogen; an alkyl group having up to 6 carbon atoms; an alkoxy group having up to 5 carbon atoms; an ester group —COOR′, where R′ contains up to 5 carbon atoms; a hydroxyl group; a phenyloxy group, optionally substituted with groups inert under reaction conditions; a trifluoromethyl group; a nitrile group; an amidic group (—CONH$_2$); an acetamidic group (—NH—CO—CH$_3$); or an acyl group —CO—R″, where R″ represents a hydrocarbon group having up to 8 carbon atoms;
R represents an alkyl group R$_1$ having up to 5 carbon atoms or an alkali metal or alkaline earth metal M.

These esters and salts (I) are obtained by reaction of a halide Y—Ar—X (II), where Ar and Y have the hereinabove defined meanings, while X is Cl, Br or I, with carbon monoxide, in an alcoholic solvent R$_1$OH (where R$_1$ is an alkyl group having up to 5 carbon atoms) at atmospheric pressure and at temperatures ranging between −10° and 60° C. in the presence of an acidity-acceptor compound and of a catalyst constituted by a cobalt complex having formula (III):

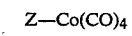

Z—Co(CO)$_4$ (III)

where Z is a group chosen among CH$_3$; CH$_2$F; CHF$_2$; CF$_3$; CH$_2$—CN; CH$_2$—COOR‴, where R‴ is an alkyl group having up to 8 carbon atoms or a benzene group, the latter optionally substituted with groups inert under reaction conditions; CH$_2$Ar′, where Ar′ is an aromatic group constituted by from one to three benzene rings optionally condensed and optionally substituted with groups inert under the reaction conditions, in particular with electron-attractor groups.

12 Claims, No Drawings

PROCESS FOR THE PREPARATION OF ESTERS OR SALTS OF AROMATIC OR ETHEROAROMATIC ACIDS

The present invention relates to a process for the preparation of esters or salts of aromatic or etheroaromatic acids. More particularly, it relates to a process for the preparation of esters or salts corresponding to formula (I):

$$Y\text{—}Ar\text{—}CO\text{—}OR \qquad (I)$$

where:

Ar represents an aromatic group constituted by one or more benzene rings, optionally condensed or by an etheroaromatic nucleus optionally condensed with one or more benzene rings Y represents from zero to more substituents, equal or different, chosen among a halogen; an alkyl group having up to 6 carbon atoms; an alkoxy group having up to 5 carbon atoms; an ester group —COOR', where R' contains up to 5 carbon atoms; an hydroxyl group; a phenyloxy group optionally substituted with groups inert under the reaction conditions; a trifluoromethyl group; a nitrile group; an amidic group (—CONH$_2$); an acetamidic group (—NH—CO—CH$_3$); or an acyl group —CO—R″, where R″ represents a hydrocarbon group having up to 8 carbon atoms R represents an alkyl group R$_1$ having up to 5 carbon atoms or an alkali metal or alkaline earth metal M.

Said esters and their corresponding acids find various applications. In fact they can be used, for example, in the preparation of alkydic resins (benzoic acid), of dyes and pigments (naphthoic acids), of azo-dyes (anthranilic acid), and in the field of plasticizing agents (esters of phthalic acid with higher alcohols).

Processes for the preparation of arylic carboxylic acids and their esters by carbonylation of aryl halides with carbon monoxide in the presence of a transition metal, for instance Ni, Pd or Pt, have been described. The reaction generally requires the use of high pressures and temperatures; these difficult working conditions negatively affect the economy of said processes, making them scarcely interesting for industry.

A variant of the above-mentioned processes comprises the use of Ni(CO)$_4$ catalysts and of special dipolar protonless solvents associated with basic compounds, which allow one to attain milder working conditions. The use of Ni(CO)$_4$ as catalyst, considering its high volatility and toxicity, compromises the commercial interest for the process; another inconvenience of that process itself lies in the use of expensive solvents.

It has also been proposed to perform carbonylation of aromatic halides in the presence of palladium catalysts with phosphinic ligands, both in homogeneous phase and in phase-transfer conditions. The high cost of the catalyst and the use of phosphinic ligands make this process poorly advantageous from the economic viewpoint.

Recently, for said carbonylation reaction of aromatic halides the use of catalytic systems constituted by cobalt salts, alcoholates, and sodium hydride has been reported; the use of cobalt carbonyl with simultaneous irradiation with UV light has also been proposed: these are mainly scientific methods for which, at the present time, it is difficult to foresee concrete opportunities of commercial application.

An aim of the present invention is to supply a simple and economic process for the preparation of esters or salts of aromatic or etheroaromatic acids having formula (I), avoiding the drawbacks of the above-mentioned processes.

Another aim is to supply a process which allows one to work at ambient temperature, or a temperature near ambient, and at atmospheric pressure.

Another aim is to supply a process wherein an easy-to-be-prepared non-toxic catalyst can be used.

Another aim is to supply a process giving high selectivity with respect to the desired product.

Said aims and still others are achieved by the process of the present invention for the preparation of esters or salts by aromatic or etheroaromatic acids having the formula Y—Ar—CO—OR (I), wherein a halide of formula (II)

$$Y\text{—}Ar\text{—}X \qquad (II)$$

where Ar and Y have the hereinabove defined meaning, while X is Cl, Br or I, is made to react with carbon monoxide in an alcoholic solvent R$_1$OH (where R$_1$ is an alkyl group having up to 5 carbon atoms) at atmospheric pressure and at temperatures ranging between $-10°$ and $60°$ C. in the presence of an acidity-acceptor compound and of a catalyst constituted by a cobalt complex having formula (III):

$$Z\text{—}Co(CO)_4 \qquad (III)$$

where Z is a group chosen among CH$_3$; CH$_2$F; CHF$_2$; CF$_3$; CH$_2$CN; CH$_2$—COOR‴, where R‴ is an alkyl group having up to 8 carbon atoms or a benzene group, the latter optionally substituted with groups inert under the reaction conditions; CH$_2$—Ar', where Ar' is an aromatic group constituted by from one to three benzene rings optionally condensed and optionally substituted with groups inert under the reaction conditions, and in particular with electron-attractor groups.

The reaction gives rise to the formation of esters or salts, in function of the nature of the acidity-acceptor compound, according to the reactions hereunder indicated:

$$Y\text{—}Ar\text{—}X + CO + 2 MOH \rightarrow Y\text{—}Ar\text{—}COOM + MX + H_2O \qquad (1)$$

$$Y\text{—}Ar\text{—}X + CO + R_1OH + B \rightarrow Y\text{—}Ar\text{—}COOR_1 + BHX \qquad (2)$$

$$Y\text{—}Ar\text{—}X + CO + R_1O \rightarrow Y\text{—}Ar\text{—}COOR_1 + X^- \qquad (3)$$

In the reaction (1) an alkali metal or alkaline-earth metal oxide or hydroxide is present, schematically represented by formula MOH. NaOH, KOH and CaO are among the preferred MOH compounds.

In the reaction (2) a weaker inorganic base B is present, preferably Na$_2$CO$_3$ or K$_2$CO$_3$. In this case, the solvent R$_1$OH, where R$_1$ is an alkyl group having up to 5 carbon atoms, is one of the reagents.

In the reaction (3), an alcoholate R$_1$O$^-$ is used, derived from the alcohol R$_1$OH used as solvent.

The catalysts Z—Co(CO)$_4$ (III) are mainly known substances in themselves, described in the following publications:

W. Hieber and others, Z. Naturforsch., 13b, 192–4 (1958)

W. Hieber and others, Z. Naturforsch., 16b, 229–31 (1961)

E. Lindner and others, Chem. Ber., 107, 1444–1455 (1974)

V. Galamb and others, Journal of Organometallic Chemistry, 209 (1981) 183–195

V. Galamb and others, J. Chem. Soc., Chem. Commun., (1982) 487–488

The process for the preparation of catalysts, too, is described in said publications. Usually they are obtained by reaction, generally in ether solvent, of the alkali metal salts of cobalt hydrocarbonyl, with the corresponding organic halides having formula (IV):

Z—X     (IV)

where Z and X have the hereinabove indicated meaning, or with the anhydrides having formula (V):

Z—CO—O—CO—Z     (V)

where Z have the hereabove indicated meaning.

When Z is a $CH_2$—COOR''' group, R''' is an alkyl group having up to 8 carbon atoms or a benzene group, the latter optionally substituted with groups inert under the reaction conditions; in the latter case, there are preferably from 1 to 3 inert groups, equal or different, chosen in particular among a hydrocarbon group having up to 8 carbon atoms, a methoxy group, a phenoxy group, and an ester group containing up to 4 carbon atoms.

When Z is a $CH_2$—Ar' group, Ar' is an aromatic group constituted by from one to three benzene rings optionally condensed and optionally substituted with groups inert under the reaction conditions, in particular with electron-attractor groups. The inert groups includes those already defined hereinbelow as well as the electron-attractor groups; the latter groups are preferred: for instance, fluorine, $CF_3$, chromotricarbonyl $Cr(CO)_3$ group and, restricted to the case of benzene nuclei, chlorine are suitable (chlorine, in fact, is not reactive under reaction conditions when it is present on a benzene nucleus). The substituent groups are equal or different and, preferably, there are 1 to 3 of them for each benzene ring. Preferably, there are from 1 to 2 benzene rings.

The starting halide Y—Ar—X (II) can contain more than one reactive halogen: in this case more than one —COOR group can replace a halogen: hence, starting for example from p-dibromobenzene, a salt or an ester of terephthalic acid is obtained.

In the halide (II), Ar represents an aromatic group constituted by one or more benzene rings, optionally condensed, or an etheroaromatic nucleus optionally condensed with one or more benzene rings.

When Ar is an aromatic group with more benzene rings, said rings may be linked to each other, for instance through a direct carbon-carbon link; the rings can be condensed as well. Preferably the Ar group contains from one to three benzene rings.

When Ar is an etheroaromatic nucleus, one or more atoms chosen among N, O and S may be present in it; for example, pyridine, furane and thiophene nuclei are suitable. The etheroaromatic nucleus may be condensed with one or more benzene nuclei; in this case, there are preferably from 1 to 3 of them.

In the halide (II), Y represents from zero to more substituents; preferably there are from 0 to 4 of them.

When in the halide (II) Y is a phenyloxy group optionally substituted with groups inert under the reaction conditions, these inert groups, equal or different, are those already defined when dealing with the Z=$CH_2$—COOR''' group; preferably there are from 1 to 4 of them.

Good results have been obtained for instance with the following halides: 2-chloronaphthalene, 2-chlorothiophene, bromobenzene, 1-chloronaphthaline, 4-bromotoluene, 3-bromoanisol, p-dibromobenzene, 4-chlorobromobenzene, 2-chlorobromobenzene, 3-chlorobromobenzene, methyl 2-chlorobenzoate, 2-bromothiophene, 2-bromoacetoanilide, 3-bromopyridine, 3-bromofurane, 2-hydroxy-6-bromonaphthalene.

The alcoholic solvent $R_1OH$ is an alkyl alcohol containing up to 5 carbon atoms. It is preferably chosen among methyl, ethyl and isopropyl alcohol.

The reaction is carried out at atmospheric pressure and at temperatures ranging between $-10°$ and $60°$ C.; it is preferably performed at temperatures ranging between $0°$ and $40°$ C. The catalyst, dissolved in a suitable solvent, is preferably added gradually into the reactor containing the other reagents and kept under CO atmosphere; ethers, in particular ethyl ether, hydrocarbons and $R_1OH$ alcohols are, for example, suitable solvents for the catalyst.

When $R_1O-$ alcoholate is used, the latter may be prepared separately or produced in "in situ" by reaction of $R_1$ OH alcohol with the alkali metal, in particular sodium.

The molar ratio between halide (II) and catalyst (III) may vary within wide limits. For example, the ratio ranges between 20:1 and 300:1. It is preferably within 20:1 to 200:1.

The acidity-acceptor compound is generally introduced according to a substantially stoichiometric ratio with respect to halide (II), according to reaction (1), (2) or (3); however an excess amount may be used as well, up to approximately 50% with respect to the stoichiometry.

To complete the reaction requires generally from 1 to 12 hours, according to the temperature, the concentration of reagents, the nature of the halide (II), and the speed at which the solution containing the catalyst is added.

The process may be effectively performed as follows: the solvent, the acidity-acceptor compound and halide (II) are introduced, in a CO atmosphere, into a reactor equipped with stirrer, thermometer and condenser. Once the mixture has reached the desired temperature, the predetermined amount of catalyst, dissolved in a suitable solvent, is added gradually under stirring. During the catalyst addition, the reaction progress is indicated by the absorption of carbon monoxide; the reaction ends when said absorption ceases.

The aromatic or etheroaromatic acid may be obtained from its salt or from its ester by known methods. For example, in case the salt is obtained, water is added and the mixture is acidified with a mineral acid, for instance HCl. The acid is extracted with a solvent, for instance ether. The organic phase thus obtained is in its turn extracted with an aqueous solution of sodium bicarbonate, which is acidified and extracted with ether, which, after evaporation, supplies the acid that can be purified using known methods.

In case an ester is obtained, it is for example possible to proceed as follows: the mixture is diluted with water, acidified and then extracted with ether. After ether evaporation, the ester is isolated with known techniques (for example, by distillation or crystallization) or it can be saponified under acid or basic conditions to give the acid.

The following examples are reported in order still better to illustrate the present invention:

EXAMPLE 1

30 ml methyl alcohol and 1 g metal sodium are introduced under CO atmosphere into a 100 ml reactor equipped with magnetic stirrer, thermometer, condenser, and dropping funnel. When all the sodium has reacted, 7.14 g 1-chloronaphthalene are introduced. The temperature is set at 25° C. and a solution of 0.103 g (ethoxy carbonyl)-methyl-cobalt tetracarbonyl

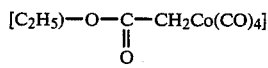

in 5 ml ethyl ether are introduced through the dropping funnel for one hour.

The solution is left under stirring at 25° C. until carbon monoxide absorption is over (approximately 2 hours), then the reaction mixture is saponified by adding 3 g NaOH and 20 ml water and kept boiling for approximately 2 hours. After cooling, water is added, acidification is carried out with concentrated HCl, and extraction is carried out with ether. The organic phase is extracted with sodium bicarbonate-saturated solution and then the aqueous layer is reacidified and finally extracted with ether. By evaporation of the solvent under vacuum, 3.75 g 1-naphthoic acid are obtained. The remainder is non-reacted product. The number of CO moles introduced into the product per mole of Co is 54.7.

EXAMPLES 2-24

Using the same equipment as for Example 1, the following examples reported in the Table below are carried out with the results shown.

| Test | Substrate (g) | Catalyst (g) | Solvent | Base (g) | Temperature °C. | Product (g) | Number of CO moles introduced into the product per Co mole |
|---|---|---|---|---|---|---|---|
| 2 | ⌬—Br (3.4) | C$_2$H$_5$O—C(O)—CH$_2$Co(CO)$_4$ (0.08) | CH$_3$OH | NaOCH$_3$ (2.3) | 17 | ⌬—COOCH$_3$ (2.53) | 26 |
| 3 | ⌬—Br (1.6) | FCH$_2$—Co(CO)$_4$ (0.057) | CH$_3$OH | NaOCH$_3$ (0.82) | 22 | ⌬—COOCH$_3$ (0.91) | 24 |
| 4 | ⌬—Br (3.75) | C$_2$H$_5$OCO—CH$_2$Co(CO)$_4$ (0.119) | CH$_3$OH | NaOCH$_3$ (2.5) | 25 | ⌬—COOCH$_3$ (2.00) | 32 |
| 5 | ⌬—Br (3.75) | C$_2$H$_5$OCOCH$_2$Co(CO)$_4$ (0.095) | CH$_3$OH | NaOH (2.5) | 25 | ⌬—COOH (1.2) | 27 |
| 6 | ⌬—Br, OCH$_3$ (4) | C$_2$H$_5$OCOCH$_2$Co(CO)$_4$ (0.072) | CH$_3$OH | NaOCH$_3$ (2.0) | 25 | ⌬—COOCH$_3$, OCH$_3$ (2.3) | 49 |
| 7 | naphthyl-Cl (7.14) | FCH$_2$Co(CO)$_4$ (0.098) | CH$_3$OH | NaOCH$_3$ (2.3) | 25 | naphthyl-COOCH$_3$ (4.2) | 47 |
| 8 | naphthyl-Cl (7.14) | FCH$_2$Co(CO)$_4$ (0.112) | C$_2$H$_5$OH | NaOC$_2$H$_5$ (3.0) | 25 | naphthyl-COOC$_2$H$_5$ (3.7) | 34 |

-continued

| Test | Substrate (g) | Catalyst (g) | Solvent | Base (g) | Temperature °C. | Product (g) | Number of CO moles introduced into the product per Co mole |
|---|---|---|---|---|---|---|---|
| 9 | Cl-naphthalene (7.14) | C₂H₅OCOCH₂Co(CO)₄ (0.119) | C₂H₅OH | NaOC₂H₅ (3.0) | 25 | naphthalene-COOC₂H₅ (4.65) | 50.4 |
| 10 | Cl-naphthalene (7.14) | C₂H₅OCOCH₂Co(CO)₄ (0.115) | i.C₃H₇OH | NaOC₃H₇ (3.6) | 35 | naphthalene-COOC₃H₇ (1.74) | 18.5 |
| 11 | Cl-naphthalene (7.14) | Cr(CO)₃–C₆H₅CH₂Co(CO)₄ (0.066) | CH₃OH | NaOCH₃ (2.3) | 25 | naphthalene-COOCH₃ (1.5) | 49 |
| 12 | Cl-naphthalene (7.14) | Cr(CO)₃–C₆H₅CH₂Co(CO)₄ (0.079) | CH₃OH | NaOCH₃ (2.3) | 10 | naphthalene-COOCH₃ (2.05) | 56 |
| 13 | 2-chlorothiophene (3.2) | C₂H₅OCOCH₂Co(CO)₄ (0.083) | CH₃OH | NaOCH₃ (2.3) | 25 | 2-COOCH₃-thiophene (3.0) | 65 |
| 14 | Br–C₆H₄–Br (5.2) | C₂H₅OCOCH₂Co(CO)₄ (0.144) | CH₃OH | NaOCH₃ (2.6) | 25 | (dopo saponificazione) HOOC–C₆H₄–COOH (2.8) | 60 |
| 15 | HO-naphthalene-Br (4.0) | C₂H₅OCOCH₂Co(CO)₄ (0.055) | CH₃OH | NaOCH₃ (2.3) | 45 | HO-naphthalene-COOCH₃ (1.30) | 30 |
| 16 | 2-Cl-naphthalene (7.14) | C₂H₅OCOCH₂Co(CO)₄ (0.178) | CH₃OH | K₂CO₃ (7.5) | 25 | 2-COOCH₃-naphthalene (2.7) | 21 |
| 17 | Cl-naphthalene (7.14) | C₂H₅OCOCH₂Co(CO)₄ (0.060) | CH₃OH | NaOCH₃ (2.3) | 0 | naphthalene-COOCH₃ (1.3) | 30 |

-continued

| Test | Substrate (g) | Catalyst (g) | Solvent | Base (g) | Temperature °C. | Product (g) | Number of CO moles introduced into the product per Co mole |
|---|---|---|---|---|---|---|---|
| 18 | 4-bromotoluene (5.95) | $C_2H_5OCO-CH_2Co(CO)_4$ (0.094) | $CH_3OH$ | $NaOCH_3$ (2.1) | 25 | methyl 4-methylbenzoate (0.61) | 11.1 |
| 19 | 3-bromofuran (6.0) | $C_2H_5OCO-CH_2Co(CO)_4$ (0.073) | $CH_3OH$ | $NaOCH_3$ (2.3) | 25 | methyl furan-3-carboxylate (2.26) | 56.4 |
| 20 | 3-bromopyridine (6.6) | $C_2H_5OCO-CH_2Co(CO)_4$ (0.087) | $CH_3OH$ | $NaOCH_3$ (2.3) | 25 | methyl pyridine-3-carboxylate (1.16) | 24.8 |
| 21 | 2-bromochlorobenzene (8.6) | $C_2H_5OCO-CH_2Co(CO)_4$ (0.083) | $CH_3OH$ | $NaOCH_3$ (2.3) | 25 | methyl 2-chlorobenzoate (3.4); dimethyl phthalate (0.570) | 80 |
| 22 | 3-bromochlorobenzene (8.6) | $C_2H_5OCO-CH_2Co(CO)_4$ (0.042) | $CH_3OH$ | $NaOCH_3$ (3.05) | 25 | methyl 3-chlorobenzoate (6.0) | 216 |
| 23 | 4-bromochlorobenzene (8.6) | $C_2H_5OCO-CH_2Co(CO)_4$ (0.074) | $CH_3OH$ | $NaOCH_3$ (3.05) | 25 | methyl 4-chlorobenzoate (5.88); dimethyl terephthalate (0.11) | 125 |
| 24 | 6-bromo-2-naphthol (3.0) | $C_2H_5OCO-CH_2Co(CO)_4$ (0.115) | $CH_3OH$ | NaOH (2.0) | 25 | 6-hydroxy-2-naphthoic acid (1.2) | 14 |
| 25 | 3-bromochlorobenzene (8.6) | $CN-CH_2-Co(CO)_4$ (0.049) | $CH_3OH$ | $NaOCH_3$ (3.05) | 25 | methyl 3-chlorobenzoate (3.26) | 82 |

What is claimed is:

1. A process for the preparation of esters or salts of aromatic or etheroaromatic acids having formula (I):

Y—Ar—CO—OR  (I)

where:
Ar represents an aromatic group constituted by one or more benzene rings, optionally condensed or an etheroaromatic nucleus optionally condensed with one or more benzene rings;
Y represents from zero to more substituents, equal or different, chosen among a halogen; an alkyl group having up to 6 carbon atoms; an alkoxy group having up to 5 carbon atoms; an ester group —COOR′, where R′ contains up to 5 carbon atoms; a hydroxyl group; a phenyloxy group optionally substituted with groups inert under the reaction conditions; a trifluoromethyl group; a nitrile group; an amidic group (—CONH$_2$); an acetamidic group (—NH—CO—CH$_3$), or an acyl group —CO—R″, where R″ represents a hydrocarbon group having up to 8 carbon atoms;
R represents an alkyl group R$_1$ having up to 5 carbon atoms or an alkali metal or alkaline-earth metal M; characterized in that a halide having formula (II)

Y—Ar—X  (II)

where Ar and Y have the hereinabove defined values, while X is Cl, Br or I, is made to react with carbon monoxide in an alcoholic solvent R$_1$OH (where R$_1$ is an alkyl group having up to 5 carbon atoms) at atmospheric pressure and at temperatures ranging between $-10°$ and $60°$ C. in the presence of an acidity-acceptor compound and of a catalyst constituted by a cobalt complex having formula (III):

Z—Co(CO)$_4$  (III)

where Z is a group chosen among CH$_3$; CH$_2$F; CHF$_2$; CF$_3$; CH$_2$—CN; CH$_2$—COOR‴, where R‴ is an alkyl group having up to 8 carbon atoms or a benzene group, the latter optionally substituted with groups inert under the reaction conditions; CH$_2$Ar′, where Ar′ is an aromatic group constituted by from one to three benzene rings optionally condensed and optionally substituted with groups inert under reaction conditions, in particular with electron-attractor groups.

2. A process according to claim 1, wherein the acidity-acceptor compound is an alkali metal or alkaline earth metal oxide or hydroxide and a salt is obtained.

3. A process according to claim 1, wherein the acidity-acceptor compound is Na$_2$CO$_3$ or K$_2$CO$_3$ and an ester is obtained.

4. A process according to claim 1, wherein the acidity-acceptor compound is an alcoholate R$_1$O$^-$ derived from an alcohol R$_1$OH used as solvent and an ester is obtained.

5. A process according to any one of the preceding claims, wherein the alcohol R$_1$OH is chosen among methyl, ethyl and isopropyl alcohol.

6. A process according to any one of claims 1 to 4, wherein the reaction is performed at temperatures ranging between $0°$ and $40°$ C.

7. A process according to any one of claims 1 to 4, wherein the catalyst, dissolved in a solvent, is added gradually into the reactor containing the other reagents and kept under CO atmosphere.

8. A process according to claim 7, wherein the catalyst solvent is an ether, a hydrocarbon, or an alcohol R$_1$OH.

9. A process according to claim 8, wherein ether is ethyl ether.

10. A process according to any one of claims 1 to 4, wherein the molar ratio between the halide (II) and the catalyst (III) ranges between 20:1 and 300:1.

11. A process according to claim 10, wherein the molar ratio between the halide (II) and the catalyst (III) is between 20:1 and 200:1.

12. A process according to any one of claims 1 to 4, wherein the molar ratio between the acidity-acceptor compound and the halide (II) ranges between the stoichiometric value and 50% excess with respect to said value.

* * * * *